(12) United States Patent
Atkinson et al.

(10) Patent No.: US 8,703,843 B2
(45) Date of Patent: Apr. 22, 2014

(54) SOLVENT EXTRACTION MICROENCAPSULATION WITH TUNABLE EXTRACTION RATES

(75) Inventors: Jeffrey L. Atkinson, Helena, AL (US); Brian Keith Chambers, Pelham, AL (US)

(73) Assignee: Evonik Corporation, Parsippany, NJ (US)

( * ) Notice: Subject to any disclaimer, the term of this patent is extended or adjusted under 35 U.S.C. 154(b) by 480 days.

(21) Appl. No.: 12/557,946

(22) Filed: Sep. 11, 2009

(65) Prior Publication Data
US 2010/0063179 A1 Mar. 11, 2010

Related U.S. Application Data

(60) Provisional application No. 61/096,016, filed on Sep. 11, 2008.

(51) Int. Cl.
*C08F 6/14* (2006.01)

(52) U.S. Cl.
USPC .......... 523/332; 427/213.3; 427/213.31; 427/389.9; 428/402; 428/402.2; 428/402.24

(58) Field of Classification Search
USPC .......... 523/332; 427/213.3, 213.31, 213.32, 427/213.33, 213.36; 424/493, 497; 435/283.1, 307.1; 428/402–402.24
See application file for complete search history.

(56) References Cited

U.S. PATENT DOCUMENTS

| 4,389,330 | A  | * | 6/1983  | Tice et al. ............... 427/213.36 |
| 5,945,126 | A  |   | 8/1999  | Thanoo et al. |
| 6,219,013 | B1 |   | 4/2001  | Amano |
| 6,270,802 | B1 |   | 8/2001  | Thanoo et al. |
| 6,361,798 | B1 |   | 3/2002  | Thanoo et al. |
| 6,440,493 | B1 | * | 8/2002  | Gibson et al. ............. 427/213.3 |
| 6,471,995 | B1 | * | 10/2002 | Ramstack ................... 424/489 |
| 6,830,737 | B2 |   | 12/2004 | Ramstack |

FOREIGN PATENT DOCUMENTS

| CA | 2736780     |   | 9/2009 |
| EP | 1 277 787   | A | 1/2003 |
| EP | 09792458.3  |   | 9/2009 |
| JP | 2011-526988 |   | 9/2009 |
| WO | WO 02/26371 | A | 4/2002 |

OTHER PUBLICATIONS

Freitas S et al.: "Microencapsulation by solvent extraction/evaporation: reviewing the state of the art of microsphere preparation process technology," *Journal of Controlled Release*, Elsevier, Amsterdam, Nl, 102(2): 313-332 (2005).
International Search Report and Written Opinion issued by International Searching Authority of WIPO on Dec. 7, 2009 for Intl. App. No. PCT/US2009/05645, filed on Sep. 11, 2009 (Inventor—Atkinson et al.; Applicant—Surmodics Pharmaceuticals, Inc.; pp. 1-14).

(Continued)

*Primary Examiner* — James J Seidleck
*Assistant Examiner* — S. Camilla Pourbohloul
(74) *Attorney, Agent, or Firm* — Linda S. Li; Jason S. Ngui (57) ABSTRACT

The present disclosure relates to processes for preparing microparticles using a solvent extraction technique, including controlled addition and/or removal of the extraction phase.

12 Claims, 5 Drawing Sheets

(56) References Cited

OTHER PUBLICATIONS

International Preliminary Report on Patentabillity issued by International Bureau of WIPO on Mar. 15, 2011 for Intl. App. No. PCT/US/2009/05645, filed on Sep. 11, 2009 (Inventor—Atkinson et al.; Applicant—Surmodics Pharmaceuticals, Inc.; pp. 1-6).

Preliminary Amendment filed by Applicant on May 5, 2011 for EP Pat. App. No. 09792458.3, national phase of Intl. App. No. PCT/US/2009/05645, filed on Sep. 11, 2009 (Inventor—Atkinson et al.; Applicant—Surmodics Pharmaceuticals, Inc.; pp. 1-4).

* cited by examiner

SOLVENT EXTRACTION MICROENCAPSULATION WITH TUNABLE EXTRACTION RATES

PRIORITY CLAIM

This application claims the benefit of U.S. Provisional Application No. 61/096,016, filed Sep. 11, 2008, which is incorporated herein by this reference in its entirety.

FIELD

The present invention relates to processes for preparing microparticles using a solvent extraction technique.

BACKGROUND

Microparticles have been used to deliver a wide range of active ingredients from perfumes to pharmaceuticals. However, the ability to efficiently and effectively control the microparticle properties, including morphology, surface characteristics and polymorph characteristics, is limited. Additionally, current microencapsulation processes typically require large holding tanks for the liquid-liquid extraction of the polymer solvent from the emulsion phase. Additionally, current processes require large quantities of extraction phase in order to adequately remove the polymer solvent from the emulsion phase.

There is therefore a need for a process that can overcome these and other deficiencies.

SUMMARY

In accordance with the purposes of the disclosed materials, compositions, articles, devices, and methods, as embodied and broadly described herein, the disclosed invention, in one aspect, relates to a process for producing microparticles comprising (a) forming an emulsion comprising a first phase comprising an agent, a polymer, and a first solvent for the polymer, in a continuous process medium; and (b) contacting the emulsion in situ with an extraction phase to extract the first solvent from the first phase into the extraction phase to form the microparticles; wherein a portion of the extraction phase is continuously removed and make up extraction phase fluid is added back into the extraction phase.

In another aspect, the invention relates to a process for producing microparticles comprising (a) forming an emulsion comprising a first phase comprising an agent, a polymer, and a first solvent for the polymer, in a continuous process medium; and (b) contacting the emulsion in situ with an extraction phase to extract the first solvent from the first phase into the extraction phase to form the microparticles; wherein extraction phase fluid is added into the extraction phase over time during step (b) such that the extraction ratio increases over time during step (b).

Additional advantages will be set forth in part in the description that follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below. Like numbers represent the same elements throughout the figures.

DETAILED DESCRIPTION

Before the present processes are disclosed and described, it is to be understood that the aspects described herein are not limited to specific processes, compounds, synthetic methods, articles, devices, or uses as such can, of course, vary. It is also to be understood that the terminology used herein is for the purpose of describing particular aspects only and, unless specifically defined herein, is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

It must be noted that, as used in the specification and the appended claims, the singular forms "a," "an" and "the" include plural referents unless the context clearly dictates otherwise. Thus, for example, reference to "a solvent" includes mixtures of two or more such solvents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

"Polymer excipient" or "polymer" as used herein refers to homopolymer or copolymer or blends comprising homopolymers or copolymers and combination thereof that are used as the microparticle wall forming or matrix materials.

"Excipient" is used herein to include any other compound or additive that can be contained in or on the microparticle that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients. This term should be distinguished from the term "polymer excipients" as defined above.

"Agent" is used herein to refer generally to a compound that is contained in or on a microparticle composition. Agent can include a bioactive agent or an excipient. "Agent" includes a single such compound and is also intended to include a plurality of such compounds.

The term "microparticle" is used herein to include nanoparticles, microspheres, nanospheres, microcapsules, nanocapsules, and particles, in general. As such, the term microparticle refers to particles having a variety of internal structure and organizations including homogeneous matrices such as microspheres (and nanospheres) or heterogeneous core-shell matrices (such as microcapsules and nanocapsules), porous particles, multi-layer particles, among others. The term "microparticle" refers generally to particles that have sizes in the range of about 10 nanometers (nm) to about 2 mm (millimeters).

The term "extraction ratio," as used herein is defined as (a) the mass of the extraction solvent in the system times (b) the solubility coefficient of the first solvent for the polymer in the extraction solvent (expressed in grams of first polymer solvent per gram of extraction phase solvent) divided by (c) the mass of the first solvent for the polymer in the system. For example, if the extraction solvent is water, and the first solvent for the polymer is hexane, the extraction ratio is the mass of water in the system times the solubility coefficient of hexane in water divided by the mass of hexane in the system. The "system" includes the dispersed phase, the continuous process medium, and the extraction phase present during the extraction process. The theoretical minimum of extraction solvent needed to remove the polymer solvent is at a ratio of 1.0. Ratios above 1.0 represent excess extraction solvent in the system.

The processes of the present invention overcome the problems and deficiencies of prior art liquid-liquid extraction processes for preparing microparticles. Specifically, with the process of the present invention, better control of the extraction and rate of extraction of the solvent from the microdroplets formed in the emulsion is achieved. Specifically, by drawing off the extraction phase from the process and either (a) purifying the drawn-off extraction phase and recycling it back to the extraction process as make-up extraction or (b) adding fresh make-up extraction, a more controlled extraction of the solvent is achieved. Thus the make-up extraction phase fluid comprises, for example, without intending to be limiting, (1) a purified recycled portion of the extraction phase wherein at least a portion of the first solvent has been removed; (2) a fresh portion of the extraction phase; or (3) a fluid comprising both (1) and (2). In one aspect, the initial extraction ratio starts out low, such as at about 1, and over the time of the extraction process, by removing solvent from the extraction system through the removal of the portion of the extraction phase, and making up with purified or fresh extraction phase, the extraction ratio increases. The initial extraction ratio refers to the extraction ratio at the outset of the process before the extraction phase is removed from the holding tank. Thus, solvent is continuously removed from the extraction process thus driving up the extraction ratio over time.

In other aspects, better control of the extraction and rate of extraction of the solvent from the microdroplets formed in the emulsion is achieved by beginning with an initial extraction ratio by contacting the emulsion with an extraction fluid and thereafter adding additional extraction fluid to the extraction phase such that the extraction ratio increases during the time in which additional extraction fluid is added to the extraction phase. In this aspect, the initial extraction ratio refers to the extraction ratio at the outset of the process before additional extraction fluid is added to the holding tank. This aspect of the invention allows for, inter alia, the tuning of release rates, e.g., forming microparticles having faster or slower release rates, depending on the exact mode of extraction.

Step (a) of forming an emulsion can be done by any method. A first phase comprising an agent, a polymer, and a first solvent for the polymer forms a dispersed phase. The dispersed phase is then mixed with a continuous process medium, which is also known as the continuous phase, to form an emulsion. This emulsion can be a single emulsion or a double emulsion. In a double emulsion, the agent is not fully soluble in the polymer solvent.

The emulsion from step (a) is contacted in situ with an extraction phase. Contacting of the extraction phase with the emulsion causes the solvent for the polymer to be extracted into the extraction phase. With the removal of the solvent for the polymer, microparticles are formed.

The emulsion is mixed with the extraction phase in an in situ process. By in situ, it is intended that the extraction phase is directly contacted with and mixed with all or substantially all of the emulsion. The extraction of the solvent out of the emulsion does not take place by removing the continuous phase from the emulsion into a separate unit operation to where solvent is extracted out of the continuous phase as is shown in U.S. Pat. No. 6,471,995. The extraction takes place directly in the emulsion-extraction phase holding tank with the emulsion being intimately contacted and mixed with the extraction phase. The processes herein are also to be distinguished over the use of a membrane in the holding tank to separate out solvent, as is shown in U.S. Pat. No. 6,471,995.

The solvent extraction is initiated but a complete extraction is not performed initially. Subsequently, the extraction medium is removed and replaced to further extract the polymer solvent from the emulsion. Alternatively, the extraction medium is not removed and additional extraction fluid is simply added to the medium to thereby increase the extraction ratio such that a complete extraction can be performed.

In one embodiment, a portion of the extraction phase is continuously removed from the emulsion-extraction phase system. This portion of the extraction phase that is removed contains some of the extracted solvent for the polymer. Thus, by removing a portion of the extraction phase, a portion of the solvent for the polymer is also removed from the system. Extraction phase is added back into the emulsion-extraction phase system to typically keep the overall volume constant. This extraction phase is added back to the emulsion-extraction phase system either by purifying the extraction phase of the extracted solvent and returning the purified extraction phase back into the system or by adding make-up fresh extraction phase. In another aspect, both a purified recycled portion of the extraction phase and the fresh portion of an extraction phase is added back to the emulsion-extraction phase system.

An advantage of this system is that the initial extraction ratio can be lower than is typically used in a liquid-liquid emulsion-extraction phase system. Over time as the solvent is removed from the system by removing a portion of the extraction phase containing the extracted solvent, the extraction ratio increases due to less solvent being in the system with the same overall amount of extraction phase. In another aspect, the extraction ratio is increased by increasing the amount of extraction phase in the overall system. The instant invention is to be contrasted with processes where the extraction phase is added all at once to the emulsion. In that system, the extraction ratio is at its final ratio at the outset of the process.

In various aspects, the initial extraction ratio is greater than 0.5, greater than 0.8, greater than 0.9, greater than 1.0, greater than 1.1, greater than 1.25, or greater than 1.5. In other aspects, the initial extraction ratio is less than 10, less than or equal to 5.0, less than or equal to 4.0, less than or equal to 3.0, less than or equal to 2.5, or less than or equal to 2.0. In other aspects, the initial extraction ratio is greater than 1 and less than or equal to 4.0, greater than 1 and less than or equal to 3, greater than 1 and less than or equal to 2.5, or greater than 1 and less than or equal to 2.0.

The agents, polymers, first solvent for the polymer, continuous process medium, extraction phase and extraction solvent are those typically used in any liquid-liquid extraction process to form microparticles. In one aspect, the extraction phase fluid comprises a single solvent for extracting the first solvent for the polymer or comprises two or more co-solvents for extracting the first solvent for the polymer. Different polymer non-solvents (i.e., extraction phase), mixtures of solvents and polymer non-solvents and/or reactants for surface modification/conjugation may be used during the extraction process to produce different extraction rates, microparticle morphology, surface modification and polymorphs of crystalline drugs and/or polymers. In one aspect, the extraction phase comprises water and in another aspect substantially comprises water.

Figure 1:
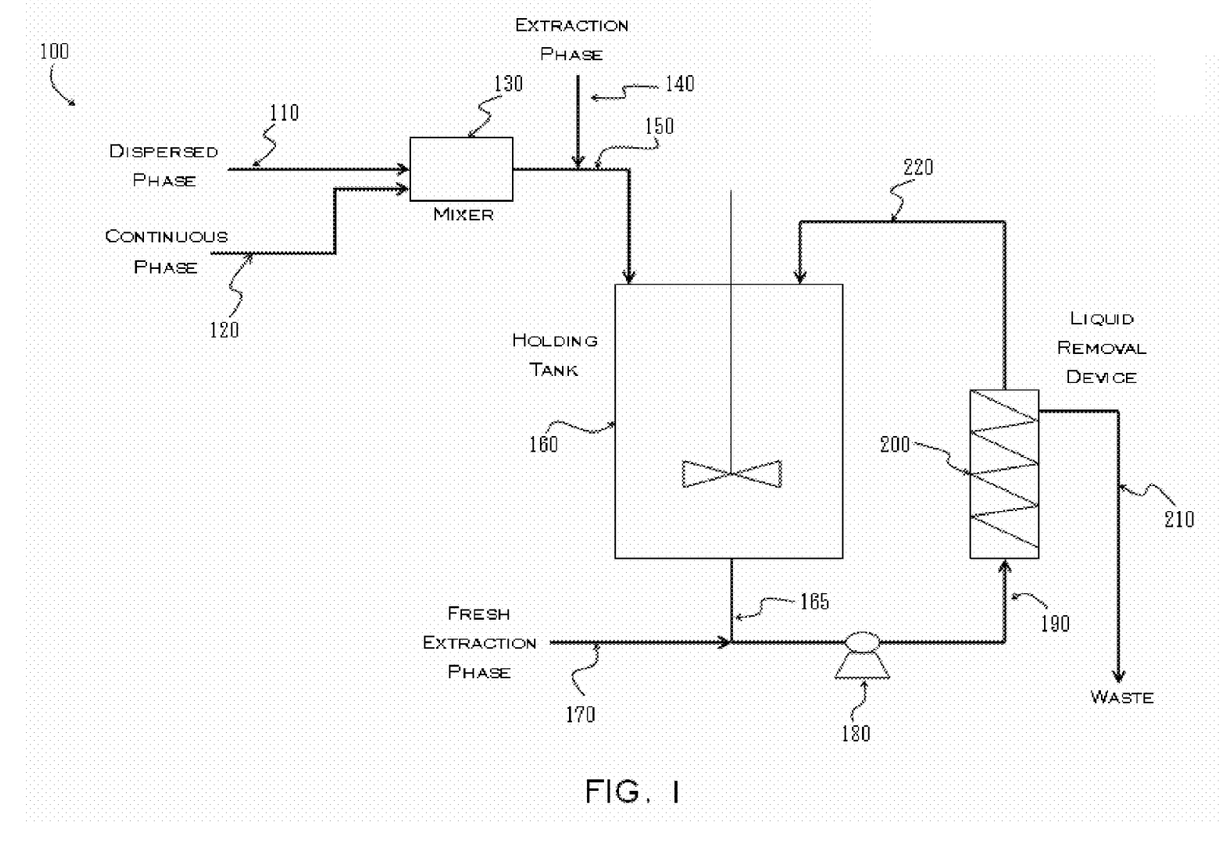
FIG. 1 shows one aspect of the apparatus and process of the present invention for preparing microparticles by a liquid-liquid extraction and an extraction phase purification and recycle loop.

Turning now to the accompanying figures, the methods and apparatuses of various aspects of the invention will be described. With reference to FIG. 1, a system 100 is shown for preparing microparticles in accordance with one aspect of the present invention. An emulsion is formed comprising a first phase or dispersed phase in a continuous process medium or continuous phase. The dispersed phase is fed through line 110 and the continuous phase is fed through line 120. Lines 110 and 120 can be each fed directly to the mixer 130 or can be combined together prior to the mixer 130. The two phases are mixed in a mixer 130. Any suitable mixing type device for preparing an emulsion can be used, such as a homogenizer or static tank with propeller or impeller for example. The emulsion produced in the mixer 130 is then mixed with the extraction phase 140 and fed through line 150 into the holding tank 160.

In holding tank 160 (and in some aspects after the extraction phase mixes with the emulsion in line 150), the liquid-liquid extraction of the solvent from the emulsion into the extraction phase takes place. In a unique aspect of this invention, on a continuous basis, a portion of the extraction phase is removed from the holding tank 160 through line 165 into pump 180 and is pumped through line 190. The extraction phase that exits from the holding tank 160 at line 165 typically comprises, for example, extraction phase liquid, such as water; first solvent; a surfactant when used; and microparticles. The microparticles are typically in a suspension. The extraction phase in line 165 can be a liquid or a thin or thick liquid slurry. At this point, the removed extraction phase containing the first solvent in line 165 can be sent directly to waste (not shown). Alternatively, the removed extraction phase containing the first solvent in line 190 can be sent to a liquid removal device 200 where some liquid is removed from the extraction phase. The liquid removal device can be any device that separates the solid microparticles from the liquid stream, such as, for example, a screen, filter, cyclone, or any dewatering type device. The stream rich in the liquid removed from the extraction phase is sent to waste via line 210. The solid-concentrated extraction phase, which had some liquid removed, is recycled back to the holding tank extraction phase through line 220. Fresh extraction phase can be added, as needed, either directly to the holding tank 160 (not shown) or at any point in the recirculation loop (the recirculation loop comprising lines 165, 190 and 220; pump 180; and device 200). FIG. 1 shows, in one aspect, the fresh extraction phase is added via line 170 prior to pump 180 at line 165. In another aspect, fresh extraction phase is added to line 220 (not shown).

In one aspect, the make-up extraction phase fluid is continuously added back into the extraction phase.

Figure 2:
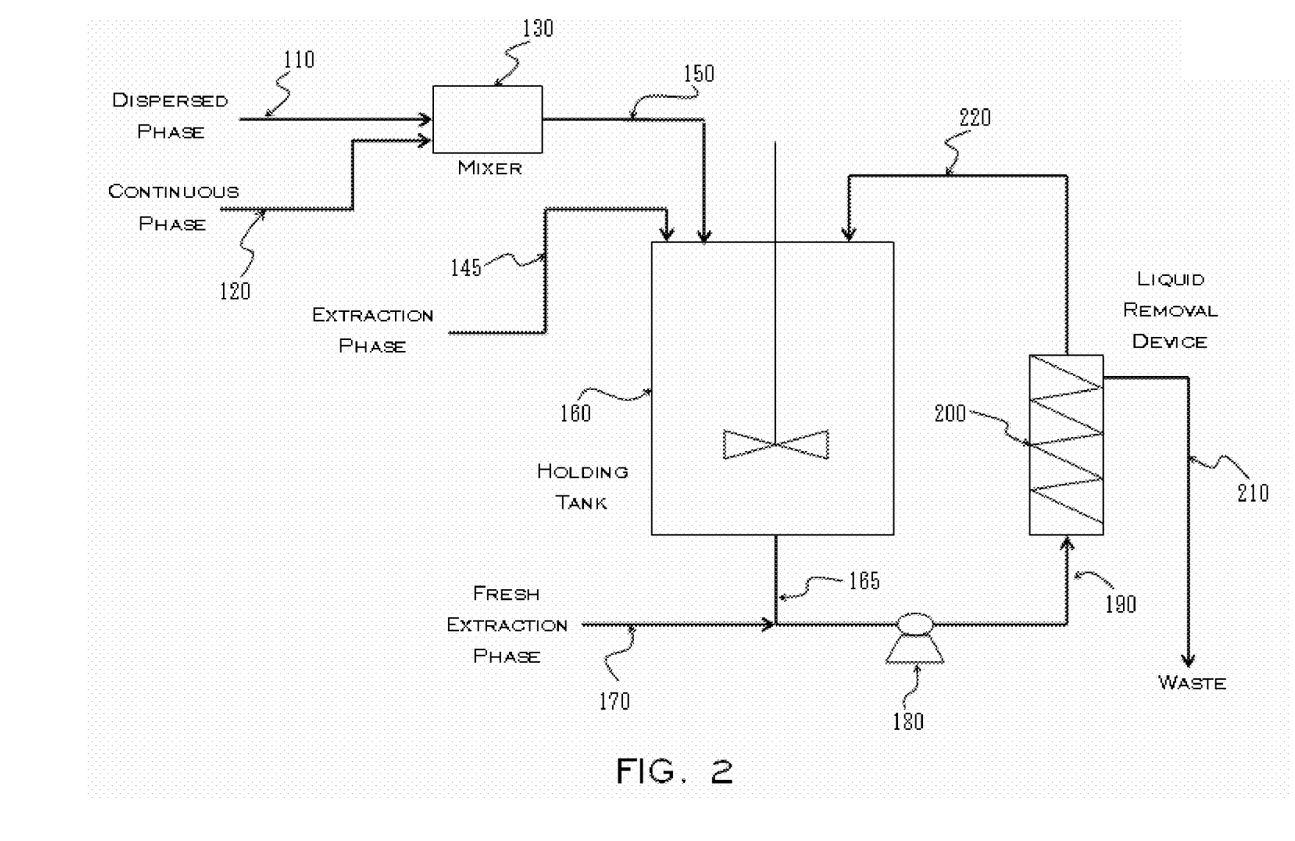
FIG. 2 shows another aspect of the apparatus and process of the present invention whereby the initial extraction phase is added directly to the holding tank.

FIG. 2 illustrates another aspect of the invention. In FIG. 2 the extraction phase is initially added to holding tank 160 through line 145. In this aspect, the holding tank starts with the necessary initial amount of extraction phase prior to the emulsion be added to the holding tank. Alternatively, in this aspect, the extraction phase can be added to the holding tank 160 through line 145 at the same time or even after the emulsion is added to the holding tank 160 through line 150.

Figure 3:
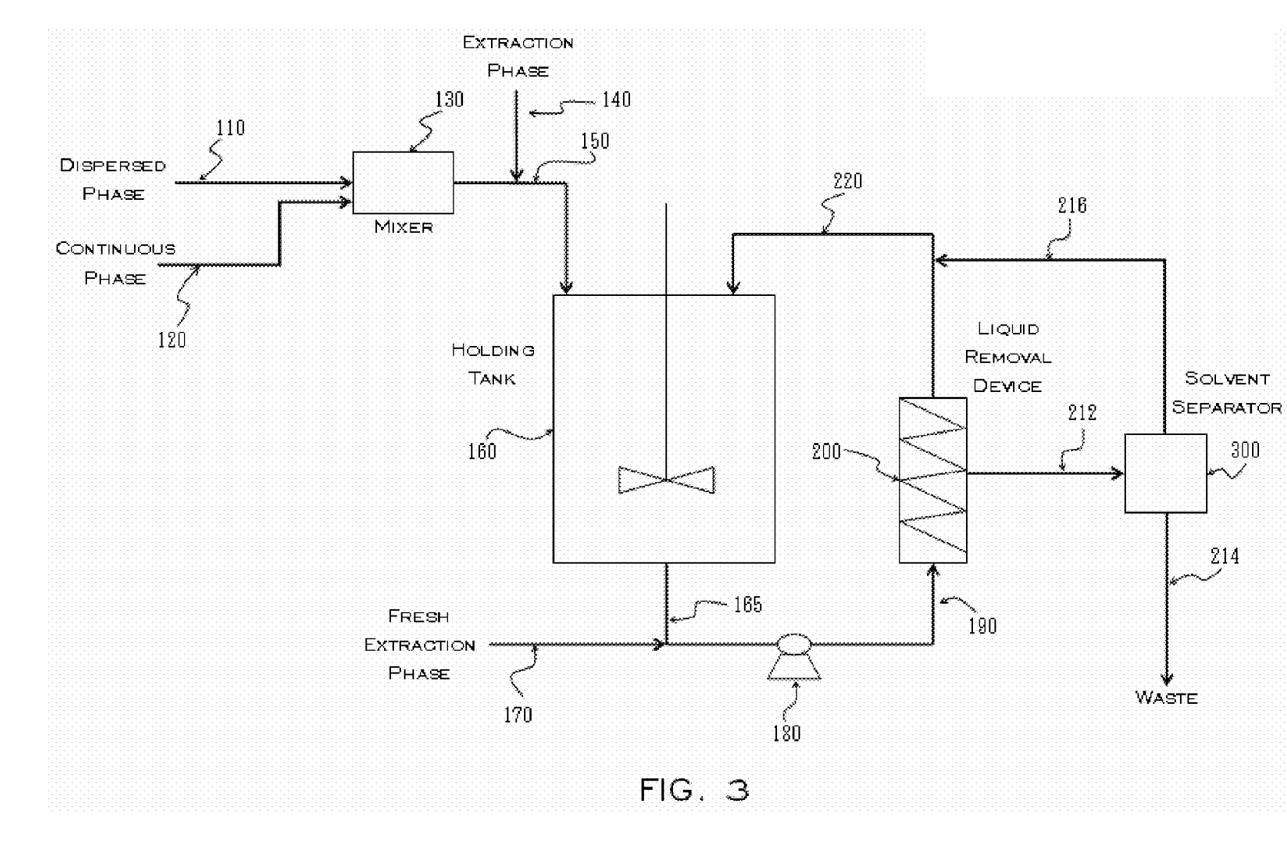
FIG. 3 shows another aspect of the apparatus and process of the present invention whereby a solvent separator is used.

FIG. 3 illustrates another aspect of the invention. In FIG. 3, rather than sending the liquid rich stream from the exit of the liquid removal device 200 directly to waste, a solvent separation step is performed. Liquid rich exit line 212 of the liquid removal device 200 is fed to a solvent separator 300. Solvent is at least partially removed and sent to waste line 214. The stream with solvent removed 216, which is richer in the extraction phase liquid than stream 212, is recycled back to the holding tank 160 by, for example, directly feeding line 216 to the holding tank (not shown) or by first combining with line 220. Examples of a solvent separator 300 include, but are not limited to, a flash evaporator or decanter.

Figure 4:
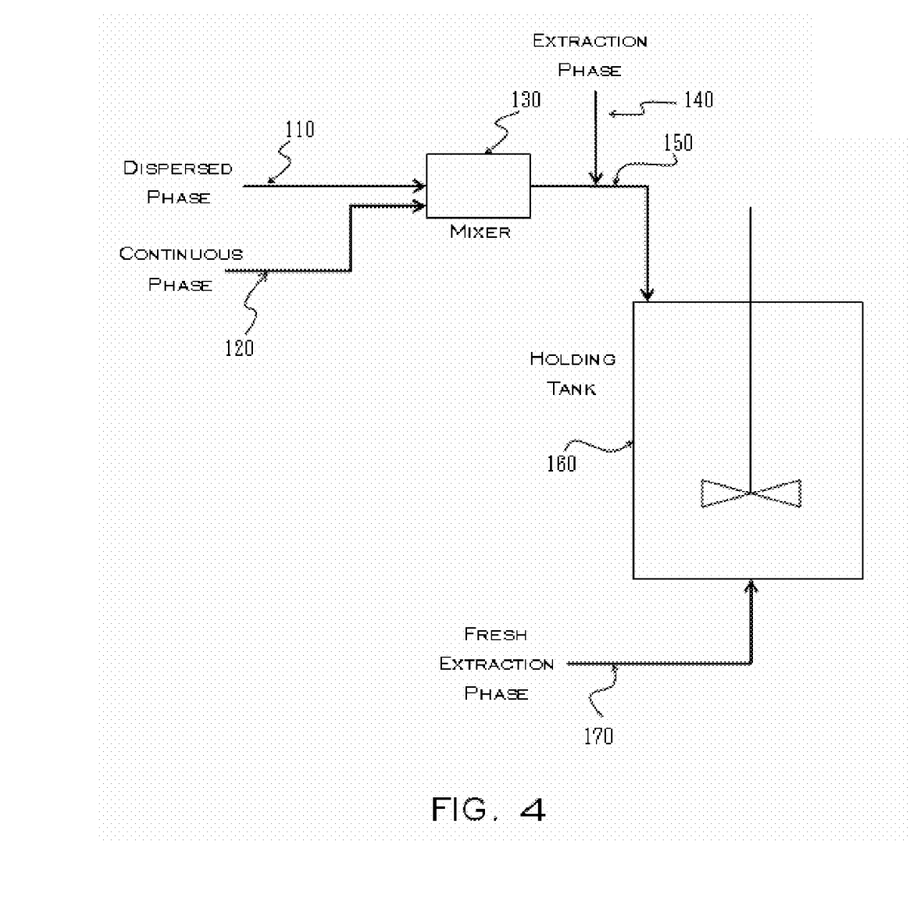
FIG. 4 shows another aspect of the apparatus and process of the present invention whereby extraction phase is added directly to the holding tank over time, such that the extraction ratio increases over time

FIG. 4 illustrates another aspect of the invention. In FIG. 4, rather than removing extraction fluid, more fresh extraction fluid is added to the holding tank to thereby increase the extraction ratio to a ratio greater than the initial extraction ratio, which initial ratio is the ratio before additional extraction fluid is added. In this embodiment, the emulsion produced in the mixer 130 is mixed with the extraction phase 140 and fed through line 150 into the holding tank 160. The amount of initial extraction phase 140 added is not enough to achieve complete extraction. Fresh extraction phase is then added through an inlet line 170 such that the extraction ratio increases. Additional extraction phase can be added through the inlet line 170 until a desired extraction ratio is achieved, which can be a ratio identified as suitable to achieve complete extraction. Additional extraction phase can also be added through line 150, or in other aspects, can be added through line 170 or any other inlet to holding take 160.

According to the process illustrated in FIG. 4, the process can be a semi-batch process, wherein the continuous process medium is present in a holding tank 160, and wherein the extraction phase fluid 140 is continuously added to the holding tank 160. Thus, in some aspects, the continuous phase is not present in a continuous process line wherein extraction phase fluid is added incrementally at multiple different points in the line. Rather, the extraction phase fluid is added into the extraction continuously to the continuous phase as a whole. To that end, in one aspect, the extraction phase fluid can be added into the holding tank over time during step (b) by using the same inlet port each time the extraction phase fluid is added, rather than adding the extraction phase fluid to the continuous phase at different points in a linear process, wherein the continuous phase moves down a process line.

The present invention provides for various advantages and features over other extraction processes. Specifically, by removing the extraction phase containing extracted solvent and adding back fresh or purified extraction phase to the emulsion-extraction phase system, controlled extraction (and rate of extraction) of the solvent from the microdroplets formed in the emulsion can be achieved. The extraction ratio can initially be set at a lower ratio than is typically used in such a process and the extraction ratio raised over time as the solvent is removed from the system. Controlled extraction of a solvent can be used to advantageously affect the microparticle morphology, surface modification, and/or polymorphs of crystalline drugs and/or polymers.

An advantage of the lower initial extraction ratio for the instant system is that less extraction phase is initially required. For water soluble agents and water as the extraction phase, this creates advantages. In that aspect, the final extraction phase ratio can be reached over time rather than at the start of the extraction. By reducing the amount of time by which the extraction is begun, less water soluble agents will diffuse out of the emulsion droplet into the water of the extraction phase. Therefore, the overall processing time can be less with the current system than is achievable in conventional systems. Additionally, the amount of extraction phase, which is typically water, can be reduced, therefore allowing for smaller processing equipment and the need to process less volume of end product water.

Additionally, the need for a large holding tank for the microparticle slurry is reduced because the microparticles can be formed with an initial low extraction ratio and then a higher extraction ratio can be achieved by adding and removing the extraction phase simultaneously. Thus, a large amount of initial extraction phase material and larger tank is avoided. A further advantage to reduced tank volumes is the reduced processing times for subsequent unit operations that are performed to the final volume of microparticle slurry such as collection, isolation, and filtration.

An additional advantage is that microparticle formation and surface modification can be performed in the same one-pot process with the controlled extraction. Additionally, rinsing and concentration of the microparticle slurry can also be performed in a one-pot process. Further, temperature adjustment to the microencapsulation slurry and extraction medium can also be used during the extraction process to produce different extraction rates, microparticle morphology, surface modification, and polymorphs of crystalline drugs and/or polymers. The temperature is easier to control in the process herein due to the smaller amount of extraction phase used throughout the system.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, pH, etc.) but some errors and deviations should be accounted for. Unless indicated otherwise, parts are parts by weight, temperature is in ° C. or is at ambient temperature, and pressure is at or near atmospheric. There are numerous variations and combinations of conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

Prophetic 0.5 g of an agent is dissolved in 10 g of a 20 wt % polymer in methylene chloride solution and homogenized with 50 g of a 2 wt % poly(vinyl acetate) in water saturated with methylene chloride solution. The emulsion is added to 700 g of an extraction phase. The microencapsule slurry is then held in a tank while additional extraction phase is added to the slurry. At the same time and rate as the extraction phase is added, extraction phase is removed using a liquid removal (dewatering) device (e.g. SWECO Pharmasep, Diafiltration column/system, self-cleaning filters, leaf filters, filter presses) (see FIG. 1). The extraction rate is controlled by the initial amount of extraction process added and the rate of addition of additional extraction phase to the microcapsule slurry.

Example 2

Prophetic 0.5 g of an agent is dissolved in 10 g of a 20 wt % polymer in methylene chloride solution and homogenized with 50 g of a 2 wt % poly(vinyl acetate) in water saturated with methylene chloride solution. The emulsion is held in a tank. Extraction phase is added to the holding tank at either a constant or variable rate until the amount of extraction phase reaches the desired extraction ratio prior to the addition of extraction phase to reach the final extraction ratio. The final extraction ratio is achieved by adding and removing extraction phase at the same rate using a liquid removal (dewatering) device (see FIG. 2). The extraction rate is controlled by the initial rate of extraction phase added and the rate of addition of additional extraction phase to the microcapsule slurry.

Example 3

Microparticle formulations containing naltrexone base were prepared using different solvent-extraction conditions. A dispersed phase (DP) solution was prepared by dissolving 0.3 grams naltrexone base into 19 grams polymer solution consisting of 20 wt % poly(DL-lactide) (0.37 dL/g) in ethyl acetate. An additional quantity of 0.95 grams of naltrexone base whose particle size had been ground to approximately 20 microns was then dispersed into this solution and was mixed with an IKA ultra-turrax T-25 with probe mixer attachment (speed 3000 rpm) for 30 seconds. After mixing, the suspension was then stirred using a magnetic stir bar and stirring with a laboratory stir plate. The resulting DP solution (suspension) was emulsified into 150 grams continuous phase (CP) solution consisting of 2 wt % aqueous PVA containing 7.4 wt % ethyl acetate. Emulsification of the DP into the CP was performed by slowly introducing the DP solution to the mixer head of a Silverson L4R-T mixer with laboratory probe style mixer head (speed setting 1000 rpm) that was immersed in the CP solution. Emulsification was performed for 30 seconds at which time the resulting emulsion was poured into a beaker containing extraction phase (EP) water. For the preparation of one formulation (batch a), the emulsion was added to a sufficient volume of EP water so as to perform full and complete extraction. In the preparation of a second formulation (batch b), the emulsion was initially added to only a small portion of the EP water and the remaining volume was then slowly added over a prescribed rate in order to reach the same final extraction as was performed on batch (a).

Batch (a) was prepared by adding the emulsion to EP water at a full extraction level using an emulsion:EP water ratio of 1:9.8 (by weight). Once full extraction level was achieved, the resulting suspension was stirred for an additional 1 hour before isolating the particles by collection across 125 micron and 20 micron test sieves. The product obtained on the 20 micron sieve was washed with 2 L water and was dried under a laminar flow hood for 48 hours.

In contrast, batch (b) was prepared by first adding the emulsion to EP water at a ratio of 1:3.9. Then sufficient water was added over a 1-hour period in order to increase the final ratio to an emulsion:EP water ratio of 1:9.8 (the same as with batch a). Once full extraction level was achieved, the suspension was stirred for an additional 1 hour before isolating, washing, and drying the particles as described for batch (a).

The drug content of these two was determined by HPLC. A known amount of sample was dissolved into glacial acetic acid then phosphate-buffered saline (PBS) was added to precipitate the polymer. The sample was then filtered to remove polymer and the resulting solution was analyzed for naltrexone by HPLC using a Waters Nova-pak 3.9×150 mm column (Waters Corporation). Chromatographic conditions were as follows: 50 µL injection volume, UV detection at 280 nm, isocratic pump method involving sodium acetate buffer: methanol: triethylamine, 75:25:0.1 v/v/v.

Figure 5:
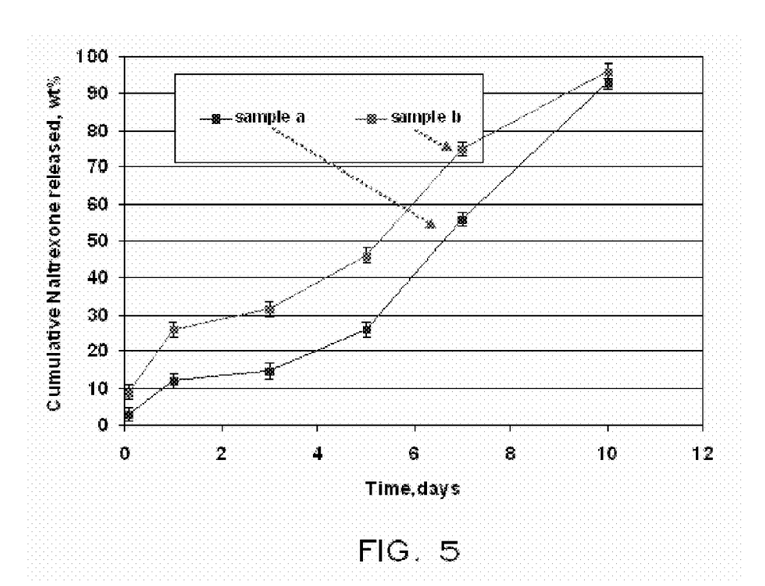
FIG. 5 shows a plot of drug release over time for microparticles prepared according to Example 3.

In vitro release rates were characterized in triplicate by measuring naltrexone release into PBS at 37° C. using HPLC. 20-30 mg sample was accurately weighed into a 150-mL glass jar and then 50-mL PBS was added. The samples were incubated at 37° C. under static conditions. At the specified time intervals, the samples were removed, mixed, and allowed to stand so the microparticles could settle to the bottom of the container. Then a 5-mL sample was removed and was replaced by 5-mL of fresh PBS solution. The containers were then placed back into the incubator until the next time point. The samples were analyzed by HPLC for drug content using the same method as described above. Cumulative naltrexone released was calculated as a mean and standard deviation and results are shown below for batch (a) and batch (b). Different initial release rates were observed between the two samples. Drug loading and batch conditions are summarized in Table 1. The plot of drug release over time is shown in FIG. 5.

TABLE 1

| Lot no | Naltrexone loading, wt % | | Batch conditions |
| --- | --- | --- | --- |
| | TCL % | Actual | Initial emulsion to EP ratio |
| Batch (a) | 25 | 13 | 1:9.8 |
| Batch (b) | 25 | 9.6 | 1:3.9 |

Example 4

Microparticle formulations containing naltrexone base were prepared using different solvent-extraction conditions as follows.

A dispersed phase (DP) solution was prepared by dissolving 0.3 grams naltrexone base into 19 grams polymer solution consisting of 20 wt % poly(DL-lactide) (0.37 dL/g) in ethyl acetate. An additional quantity of 0.95 grams of naltrexone base whose particle size had been ground to approximately 2 microns was then dispersed into this solution and was mixed as described previously. The resulting DP solution (suspension) was emulsified into 250 grams CP solution consisting of 2 wt % aqueous PVA containing 7.4 wt % ethyl acetate. Emulsification of the DP and CP was performed in a continuous manner by introducing the DP and CP solutions to the inlet port of a Silverson L4R-T mixer with inline attachment (speed setting 1000 rpm). The flow-rates for DP and CP solutions were 15 g/min and 125 g/min respectively. Different batches were prepared using different extraction conditions as follows.

One batch, batch (a), was prepared by adding the emulsion directly to sufficient EP water at an emulsion:EP water ratio of 1:9.8 (full, immediate extraction conditions). The resulting suspension was collected into a container and stirred for 1 hour after which time the microparticle product was isolated, washed, and dried as described previously.

A second batch, batch (b), was prepared by adding the emulsion directly to only sufficient EP water so as to reach an initial emulsion:EP water ratio of 1:3.9 (partial initial extraction). The resulting suspension was collected into a container and then EP water was added at a steady rate over 1 hour to reach a final ratio of 1:9.8 after which time the microparticle product was isolated, washed, and dried as described previously.

A third batch, batch (c), was prepared by adding the emulsion directly to only sufficient EP water so as to reach an initial emulsion:EP water ratio of 1:4.3. The resulting suspension was collected into a container and then EP water was added at a steady rate over approximately 5 hours to reach a final ratio of 1:9.8 after which time the microparticle product was isolated, washed, and dried as described previously.

A fourth batch, batch (d), was prepared using a combined dewatering and tunable extraction process. A DP solution was prepared by dissolving 19 grams naltrexone base into 1000 grams polymer solution consisting of 25 wt % poly(DL-lactide) (0.37 dL/g) in ethyl acetate. An additional quantity of 64 grams naltrexone base (particle size approximately 2 microns) was dispersed into the solution. The resulting DP solution (suspension) was emulsified into 8000 grams CP solution consisting of 2 wt % aqueous PVA solution containing 7.4 wt % ethyl acetate. Emulsification of the DP and CP was performed in a continuous manner by introducing the DP and CP solutions to the inlet port of a Silverson L4R-T mixer with inline attachment (speed setting 1300 rpm). The flow-rates for DP and CP solutions were 40 g/min and 250 g/min respectively. The effluent emulsion from the mixer directly to only sufficient EP water so as to reach an initial emulsion:EP water ratio of 1:3.6. The resulting suspension was collected in a suitable vessel and then EP water was added at a steady rate over 5 hours to reach a final ratio of 1:9.8 while, over the same time, the suspension was passed through a hydrocyclone apparatus (inlet pressure 50-60 psi) to partially remove effluent liquid (dewater) by retaining the underflow and discarding the overflow liquid. At the completion of the 5-hour extraction process, collection was initiated by a combined dewatering and sieving operation whereby the underflow effluent from the hydrocyclone apparatus was passed across 125-micron and 20-micron test sieves. The resulting product was washed with 10-L water and then dried under a laminar flow hood for 48 hours.

All samples were analyzed for drug content and in vitro release by methods described previously.

Figure 6:
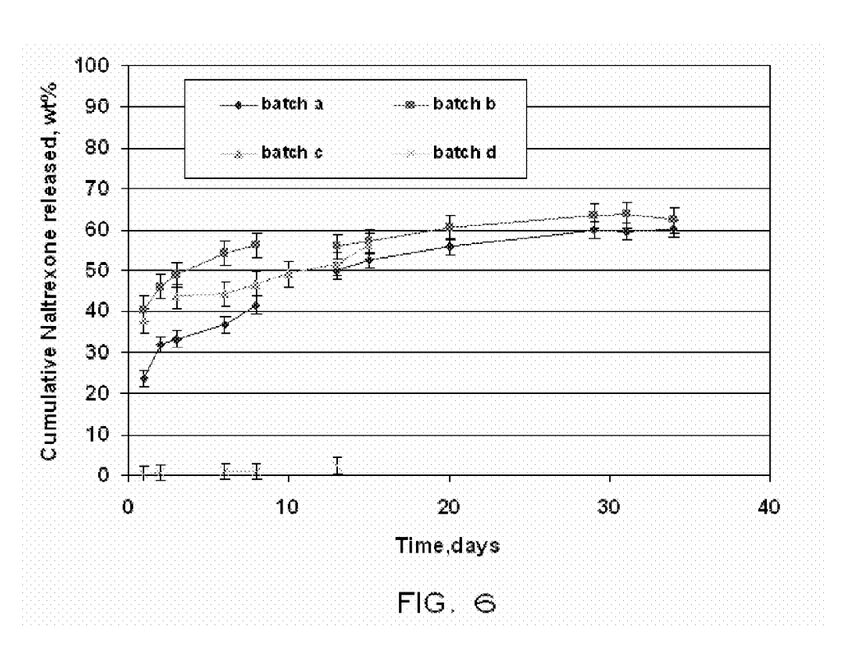
FIG. 6 shows a plot of drug release over time for microparticles prepared according to Example 4.

As demonstrated between batches (a), (b), and (c), varying the solvent-extraction conditions and extraction rates can result in variable burst and release rates over time. As demonstrated by batch (d), further combining dewatering with varying the extraction conditions can produce further changes in the overall burst and release profiles of the resulting microparticle formulation. Drug loading and batch conditions are summarized in Table 2. The plot of drug release over time is shown in FIG. 6.

TABLE 2

| Lot no | Naltrexone loading, wt % | | Batch conditions |
|---|---|---|---|
| | TCL % | Actual | Initial emulsion to EP ratio |
| Batch a | 25 | 12.4 | 1:9.8 |
| Batch b | 25 | 15.2 | 1:3.9 |
| Batch c | 25 | 14.3 | 1:4.3 |
| Batch d | 25 | 8.5 | 1:3.6 |

While particular embodiments of the present disclosure have been illustrated and described, various other changes and modifications are enabled and can be made without departing from the spirit and scope of the disclosure. It is therefore intended to cover in the appended claims all such changes and modifications that are within the scope of this disclosure.

What is claimed is:

1. A process for producing microparticles having tunable release rates comprising
   (a) forming an emulsion comprising a first phase comprising an agent, a polymer, and a first solvent for the polymer, in a continuous process medium; and
   (b) contacting the emulsion in situ with an extraction phase whereby the first solvent from the first phase is extracted into the extraction phase to form the microparticles;
   wherein a portion of the extraction phase containing the extracted first solvent and microparticles is continuously removed and make up extraction phase fluid is added back into the extraction phase, wherein the extraction ratio increases over time during step(b).

2. The process of claim 1, wherein the make up extraction phase fluid comprises:
   (1) a purified recycled portion of the extraction phase wherein at least a portion of the first solvent has been removed;
   (2) a fresh portion of the extraction phase; or
   (3) a fluid comprising both (1) and (2).

3. The process of claim 1, wherein the extraction phase comprises two or more co-solvents.

4. The process of claim 1, wherein the emulsion is a single emulsion.

5. The process of claim 1, wherein the emulsion is a double emulsion.

6. The process of claim 1, wherein the initial extraction ratio is greater than 0.5 and less than or equal to 5.0.

7. The process of claim 1, wherein the initial extraction ratio is greater than 1 and less than or equal to 3.0.

8. The process of claim 1, wherein the initial extraction ratio is greater than 1 and less than or equal to 2.5.

9. The process of claim 1, wherein the initial extraction ratio is greater than 1 and less than or equal to 2.0.

10. The process of claim 1, wherein the extraction phase substantially comprises water.

11. The process of claim 1, wherein the process is a semi-batch process, wherein the continuous process medium is present in a holding tank; and wherein the extraction phase fluid is added to the holding tank.

12. The process of claim 1, wherein the extraction phase fluid is added into the continuous phase continuously.

* * * * *